United States Patent [19]

Cooper et al.

[11] Patent Number: 4,943,498

[45] Date of Patent: Jul. 24, 1990

[54] BATTERY AND BATTERY RECEPTACLE ARRANGEMENT

[75] Inventors: Robin A. Cooper, Surrey; Barry J. Fazackerley, London, both of England

[73] Assignee: Hugh Steeper Limited, London, England

[21] Appl. No.: 397,735

[22] Filed: Aug. 23, 1989

[30] Foreign Application Priority Data

Aug. 25, 1988 [GB] United Kingdom ............... 8820230

[51] Int. Cl.⁵ .............................................. H01M 2/10
[52] U.S. Cl. ...................................... 429/97; 429/100; 429/123
[58] Field of Search ................. 429/123, 163, 96–100, 429/9

[56] References Cited

U.S. PATENT DOCUMENTS

| | | | |
|---|---|---|---|
| 3,062,911 | 11/1962 | Joy | 429/98 |
| 3,537,909 | 11/1970 | Horton | 429/98 |
| 3,864,172 | 2/1975 | Marks | 429/96 X |
| 3,999,110 | 12/1976 | Ramstrom et al. | 429/163 X |
| 4,085,253 | 4/1978 | Johnson | 429/1 |
| 4,237,202 | 12/1980 | Karpal | 429/163 X |

Primary Examiner—Anthony Skapars
Attorney, Agent, or Firm—Berman, Aisenberg & Platt

[57] ABSTRACT

A battery and battery receptacle arrangement, comprising a battery as a first part of the arrangement and a battery receptacle as a second part of the arrangement, in which at least one formation provided on one of the parts engages a corresponding formation provided on the other part when the battery is inserted in the receptacle and moved transversely therewithin, thereby to retain the battery in the receptacle in a readily releasable manner.

13 Claims, 4 Drawing Sheets

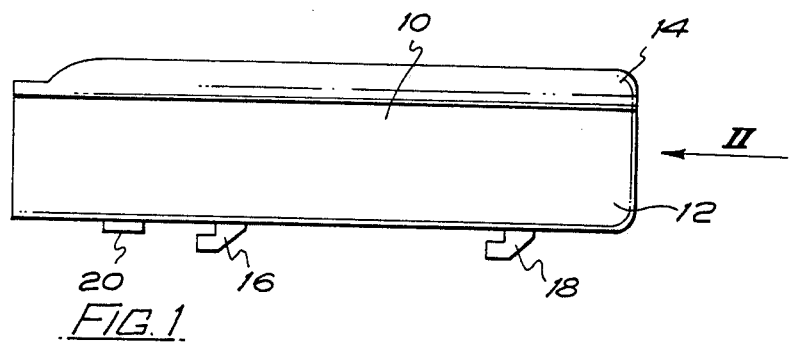
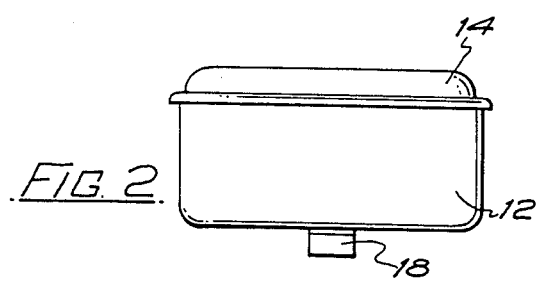
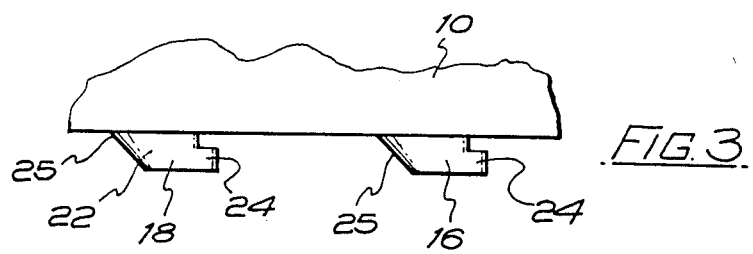
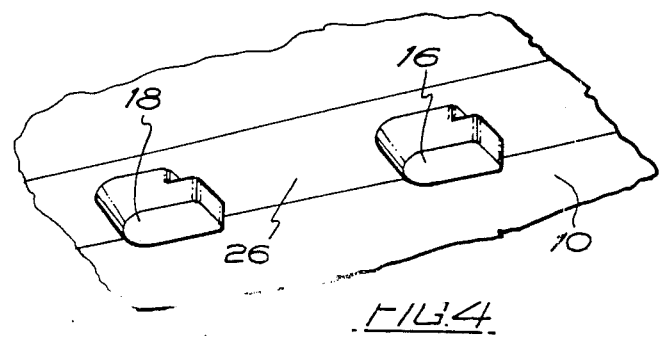

BATTERY AND BATTERY RECEPTACLE ARRANGEMENT

The present invention relates to a battery and battery receptacle arrangement, expecially but not exclusively for use in an electrically driven prosthesis.

US-A-4,072,800 discloses such an arrangement which is provided with pivot means at one end by which the battery can be pivoted into the receptacle, and snap-action means at an opposite end by which the battery is releasably held in the receptacle once it is pushed fully home. The snap-action device in such a construction is relatively complex, and the present invention seeks to provide a simpler construction.

Accordingly, the present invention is directed to a battery and battery receptacle arrangement, comprising a battery as a first part of the arrangement and a battery receptacle as a second part of the arrangement, in which at least one formation provided on one of the parts engages a corresponding formation provided on the other part when the battery is inserted in the receptacle and moved transversely therewithin, thereby to retain the battery in the receptacle in a readily releasable manner.

The or each formation provided on one of the parts may comprise a projection, and the corresponding formation may comprise a hole or recess.

In one convenient construction, the or each projection is provided on the battery casing.

Preferably, the or each projection has a transverse portion which is spaced from the battery casing or a receptacle wall, as the case may be, and which extends in a transverse direction which is transverse to the outward direction of projection, the receptacle as a whole permitting movement of the battery therewithin in a transverse direction, to enable the projection to be locked onto the receptacle or battery casing as the case may be at the hole or recess, and thereby retain the battery in a readily releasable manner.

The or each projection preferably has a simple hook construction so that it can be inserted through the hole or recess and hooked onto a portion which defines the hole or recess. Alternatively, the projection may be in the form of a stud and the hole or recess may be in the general shape of a keyhole, so that the stud is inserted into the keyhole at the wider portion thereof, and then slid along so that a neck portion of the stud extends through the narrower portion of the keyhole.

The projection and/or the hole or recess may be provided with a slanting surface that urges the projection out of engagement with the hole or recess when the battery is moved in a transverse direction within the receptacle.

A convenient shape for the battery and the receptacle is a rectangular shape, in which case the transverse direction of permitted movement of the battery within the receptacle is desirably parallel or substantially parallel to the longer sides of the rectangle.

A suitable position for the or each projection is the intended underside of the battery casing, the or each hole or recess being in the bottom of the receptacle.

One or more spring members attached to one of the parts of the arrangement may press directly or indirectly against, or be received in a hole or recess formed in, the other part of the arrangement, to resist the otherwise permitted movement of the battery within the receptacle in a transverse direction. The or each of the spring members may be metallic and effect an electrical connection between the battery and the receptacle when the battery is retained in the receptacle.

The or each spring member may be contained within the battery, to urge a slidable member, also accommodated within the battery, in a slide direction which is transverse to the said transverse direction of movement of the battery in the receptacle, and a sloping member may be fixed within the receptacle in such a position that the said slide member in the battery engages the sloping member in the receptacle when the battery is inserted therein, to resist the otherwise permitted movement of the battery within the receptacle in a transverse direction.

Advantageously, the whole or substantially the whole of the battery fits in the receptacle so that when the battery is inserted in the receptacle an outer surface of the battery casing is flush or sbstantially flush with a rim of the receptacle. Such an arrangement is particularly suitable for use in an electrically driven prosthesis. The receptacle may then be positioned to define a recess in the outer surface of the prosthesis, and at least the intended outer surface of the battery casing may be skin coloured to improve the cosmetic appearance of the prosthesis It will be appreciated that the battery can be readily removed for replacement and/or recharging. Examples of battery and battery receptacle arrangements embodying the present invention are illustrated in the accompanying drawings in which:

FIG. 1 is a side view of a battery of a first arrangement;

FIG. 2 is an end view of the battery shown in FIG. 1, viewing it in the direction of the arrow II in FIG. 1;

FIG. 3 is a more detailed representation of parts of the battery shown in FIG. 1, viewing it from the other side;

FIG. 4 is a perspective underneath view of the parts shown in FIG. 3;

Figure 10:
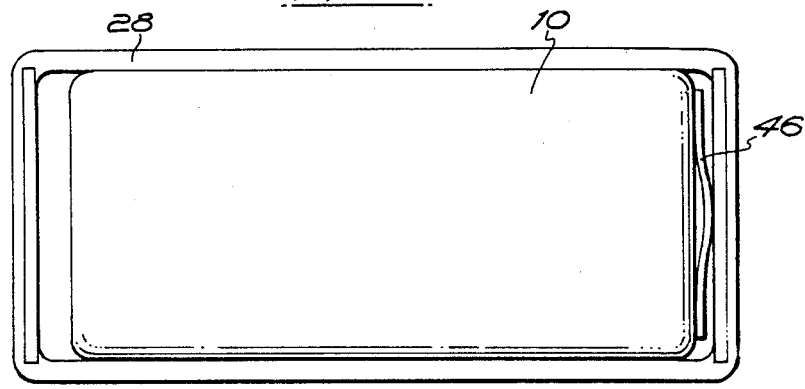
FIG. 10 shows a plan view of the arrangement shown in FIG. 9.

The battery shown in FIGS. 1 to 4 comprises a casing 10 which, when viewed from above, as shown in FIG. 10, is generally rectangular in shape. The casing 10 is made of a synthetic plastics material and is made up of a lower section 12 and an upper section 14 sealed to the lower section 12 once the contents of the battery have been inserted. Two projections 16 and 18 project downwardly from the bottom of the battery casing 10. Two metallic electrical contacts 20 (only one of which is visable in FIG. 1) also extend along the underside of the battery casing 10.

As is more evident from FIGS. 3 and 4, each projection 16 and 18 comprises a portion 22 which extends away from the battery casing, and a portion 24 which is spaced from the battery casing and extends transversly of the direction of outward projection of the portion 22. The direction in which the portion 24 extends is along an axis of the battery casing 10, generally parallel to the longer sides of the receptacle, viewing the battery as in FIG. 10. Each projection 16 and 18 is provided with a slanting surface 25 on a side of the projection opposite to that of the portion 24.

The projections 16 and 18 are attached to a fuse cover 26 of the battery casing 10, although other positions are possible.

Figure 5:
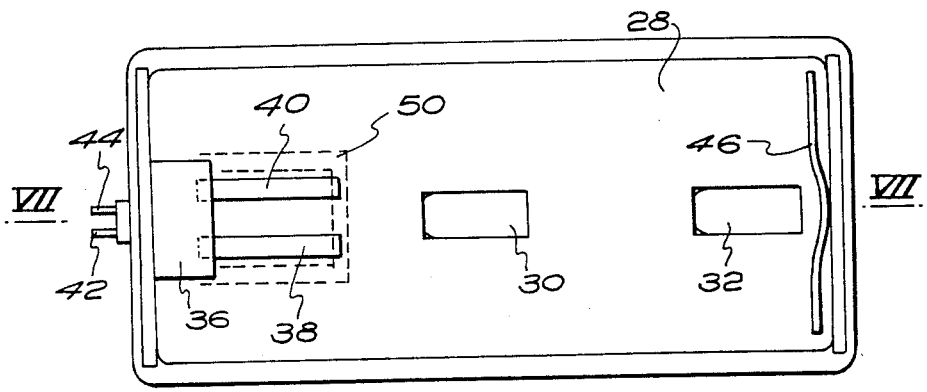
FIG. 5 is a plan view of a receptacle of the arrangement.
Figure 6:
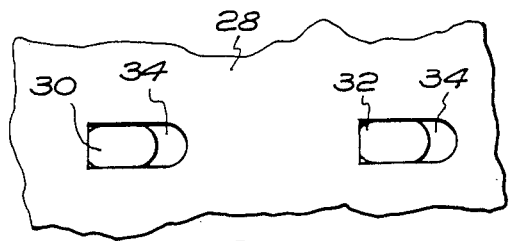
FIG. 6 is a more detailed representation of parts of the receptacle shown in FIG. 5.
Figure 7:
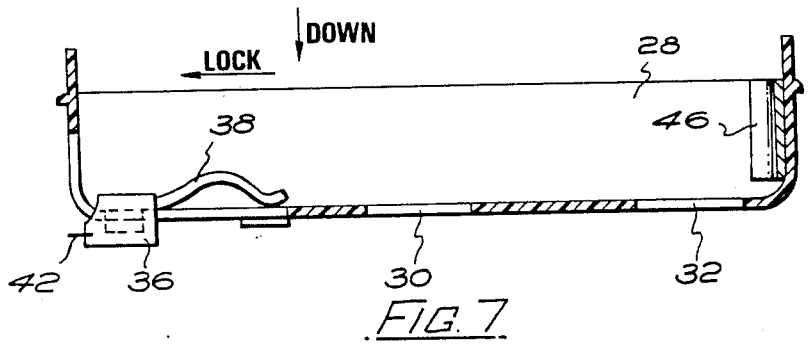
FIG. 7 shows an axial sectional view of the receptacle shown in FIG. 5 taken along the line VII—VII shown in that FIG.
Figure 8:
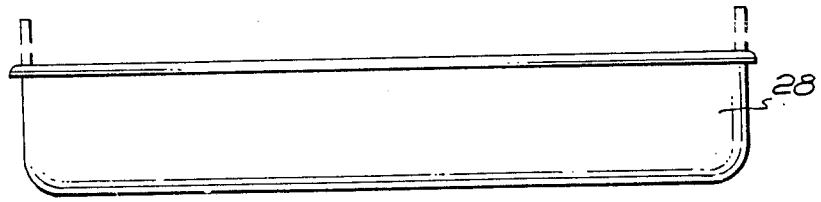
FIG. 8 is a side view of the receptacle shown in FIG. 7.

The receptacle 28 shown in FIGS. 5 to 8 also has a generally rectangular shape as viewed from above, having substantially the same width as the battery casing 10 as viewed from above, but being slightly longer than the battery casing 10. The depth of the receptacle as viewed in FIG. 7 or 8 is substantially the same as that of the battery casing as viewed in FIG. 1 or 2. Two holes 30 and 32 are formed in a bottom wall of the receptacle. The positions of the projections 16 and 18 of the battery casing 10, and have slanting surfaces 34 at respective ends thereof.

One end of the bottom of the receptacle 28 is provided with a plug 36 from which extend, within the interior of the receptacle in an axial direction along the bottom thereof, two elongate spring metal contacts 38 and 40 which are both curved so that they arch upwardly from the bottom of the receptacle. Two wires 42 and 44 extend from the plug 36 from outside of the receptacle, these wires 42 and 44 being respectively electrically connected to the contacts 38 and 40 within the plug 36.

The end of the receptacle 28 which is further from the plug 36, on the interior thereof, is provided with a spring buffer 46.

Figure 9:
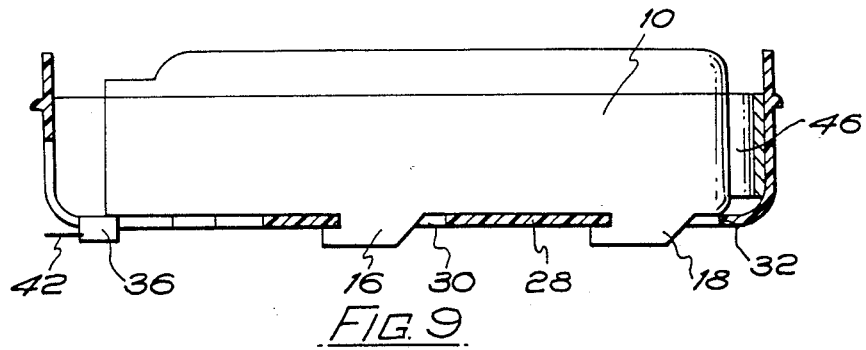
FIG. 9 is a partly axial sectional view of the arrangement with the battery releasably inserted in the receptacle.

The battery shown in FIGS. 1 to 4 is inserted in the receptacle shown in FIGS. 5 to 8 by orienting the battery so that its contacts 20 are in line with the contacts 38 and 40 of the receptacle, lowering the battery downwardly into the receptacle so that the projections 16 and 18 are inverted through the holes 30 and 32 of the receptacle and then moving the battery transversely within the receptacle in an axial direction towards the plug end of the receptacle so that the transverse portions 24 of the projections 16 and 18 engage the outer underside of the receptacle, and the contacts 20 on the battery wipe the contacts 38 and 40 during the transverse movement and are left in firm electrical contact therewith. The frictional force exerted between the contacts of the battery and the receptacle by virtue of the normally curved shape of the receptacle spring contacts may be sufficient to hold the battery in position as shown in FIG. 9. However, although the spring buffer 46 is not essential, it provides a further resistive force by urging the battery in a direction within the receptacle towards the plug end thereof. Thus axial movement of the battery in the receptacle in a direction that would release it is resisted. An additional resistance may be achieved by providing the battery casing with a recess on its underside, in the position corresponding to the box 50 shown in broken lines in FIG. 5, into which the spring contacts 38 and 40 project when the battery is inserted into the receptacle. Nonetheless, it will be appreciated that the resisting forces are readily overcome manually so that the battery can be readily released from the receptacle. In this respect, the movement of the battery away from the plug end of the receptacle causes the slanting surfaces 25 on the projections 16 and 18 to ride up the slanting surface 34 of the holes 30 and 32 to urge the battery upwardly in an outward direction from the receptacle 28.

In the modified arrangement shown in FIGS. 11 to 15, there is only one projection 16 on the underside of the battery casing 10, and one corresponding hole 30 in the bottom wall of the receptacle 28. Instead of the spring buffer 46, two helical compression springs 50 (only one of which is shown in FIGS. 11 to 15) are positioned within the battery casing 10 at one end thereof. Each spring 50 extends between a top wall of the receptacle 10 and a slidable member 52, which is free to slide up and down between an end wall 54 of the casing 10 and a partition wall 56 thereof. Each spring 50 therefore urges its slidable member 52 in a downward direction, movement of the slidable member 52 in that direction being limited by a front edge 58 of the bottom wall of the battery casing 10. The two slidable members 52 are positioned at that end of the battery casing 10 which is the one on the other side of the projection 16 from that of the transversely extending portion 24.

The receptacle 28 is provided with two sloping elements 60 spaced apart at one end thereof. The spacing between the sloping elements is the same as that between the slidable members 52 in the battery casing 10. Each sloping member 60 has a sloping face 62 which slopes downwardly from an upper surface of the member 60 and towards the hole 30.

It will be appreciated that the plug and contact construction of the first arrangement illustrated in FIGS. 1 to 10 is present in the arrangement shown in FIGS. 11 to 15, although that construction has not been shown in the latter Figures for the sake of clarity.

Figure 11:
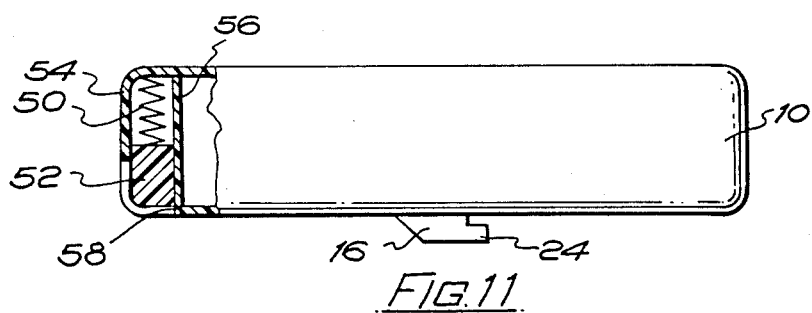
FIG. 11 is a side, partly cut-away view of a battery of a second arrangement.
Figure 12:
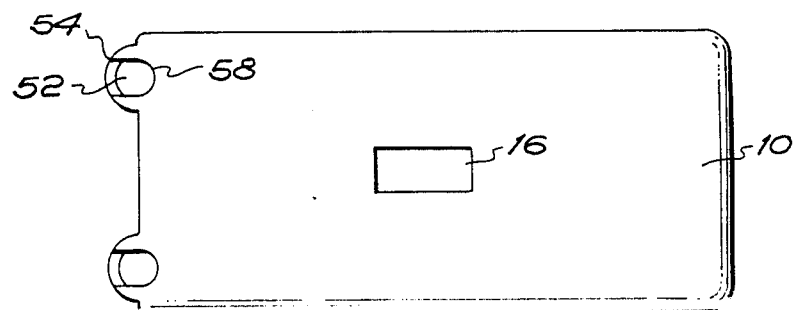
FIG. 12 is an underneath view of the battery shown in FIG. 11.
Figure 13:
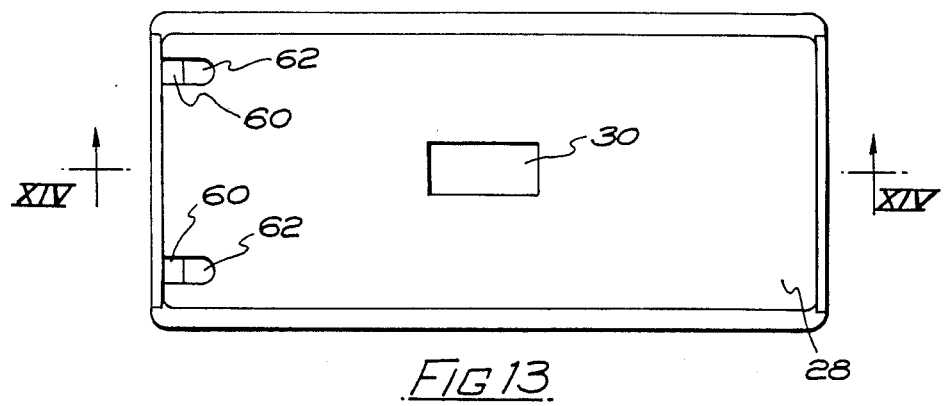
FIG. 13 is a plan view of a receptacle of the arrangement.
Figure 14:
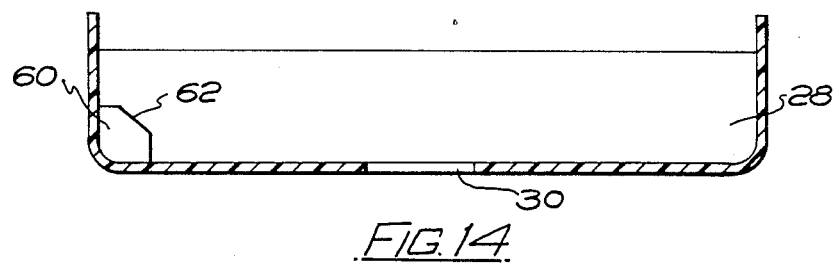
FIG. 14 shows an axial sectional view of the receptacle shown in FIG. 13 taken along the line XIV—XIV.
Figure 15:
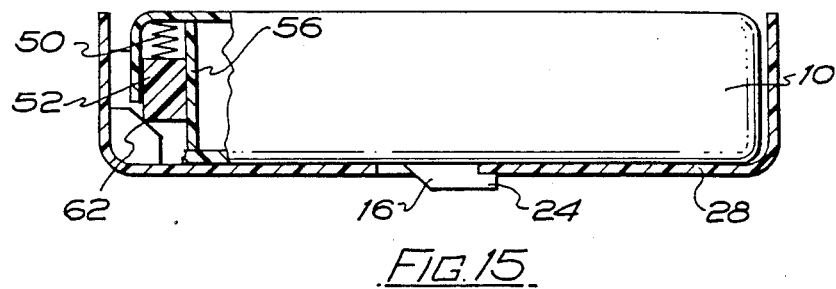
FIG. 15 shows a partly axial sectional view of the second arrangement with the battery releasably inserted in the receptacle.

When the battery casing shown in FIGS. 11 and 12 is inserted into the receptacle shown in FIGS. 13 and 14 it is dropped vertically downwardly therein so that the projection 16 passes through the hole 30 and the slidable members 52 engage the sloping elements 60. The downward force of the compression springs 50 on the slidable elements 52 urges the latter against the sloping surface 62 of the element 60, so as to urge the battery casing in a transverse direction, so that the portion 24 extends underneath the bottom wall of the receptacle 28. This inhibits movement of the battery casing 10 in an unpward direction away from the receptacle 28.

To disengage the battery casing 10 from the receptacle 29, it must first be urged in a transverse direction to disengage the portion 24 from the bottom wall of the receptacle 28, against the force of the compression springs 50, until the projection 16 can once again pass through the hole 30. It is to be noted, that once the battery casing 10 has been slid transversely in relation to the receptacle 28 in this way, the force of the springs 50 will assist in lifting the projection 16 out of the hole 30.

Numerous variations and modifications may be made to the illustrated arrangements without taking them outside the scope of the present invention. To give one example only of such a modification, projections may be provided on the receptacle and holes or recesses in the battery casing.

What we claim is:

1. A battery and battery receptacle arrangement, comprising (a) a battery as a first part of the arrangement, (b) a battery receptacle as a second part of the arrangement, (c) at least one formation provided on one of the parts, (c) a corresponding formation provided on the other part, which corresponding formation is engaged by the said at least one formation when the battery is inserted in the receptacle and moved transversely therewithin, thereby to retain the battery in the receptacle in a readily releasable manner.

2. An arrangement according to claim 1, in which the formation provided on one of the parts comprises a projection, and the corresponding formation comprises a hole.

3. An arrangement according to claim 2, in which the projection is provided on the battery casing.

4. An arrangement according to claim 2, in which the projection has a transverse portion which is spaced from the said one of the parts, and which extends in a transverse direction which is transverse to the outward direction of projection, the receptacle as a whole permitting movement of the battery therewithin in a transverse direction, to enable the projection to be locked onto the other part at the hole thereof and thereby retain the battery in a readily releasable manner.

5. An arrangement according to claim 2, which the projection has a simple hook construction so that it can be inserted through the hole and hooked onto a portion which defines the hole.

6. An arrangement according to claim 2, in which the projection is provided with a slanting surface that urges the projection out of engagement with the hole when the battery is moved in a transverse direction within the receptacle.

7. An arrangement according to claim 2, which the hole is provided with a slanting surface that urges the projection out of engagement with the hole when the battery is moved in a transverse direction within the receptacle.

8. An arrangement according to claim 1, in which both the battery and the receptacle have a rectangular shape, and in which the transverse direction of permitted movement of the battery within the receptacle is parallel or substantially parallel to the longer sides of the rectangle.

9. An arrangement according to claim 2, in which the projection is on the intended underside of the battery casing, and the hole is in the bottom of the receptacle.

10. An arrangement according to claim 1, in which at least one spring member is attached to one of the parts of the arrangement and presses against the other part of the arrangement, to resist the otherwise permitted movement of the battery within the casing in a transverse direction.

11. An arrangement according to claim 10, in which the spring member is contained within the battery, to urge a slidable member, also accommodated within the battery, in a slide direction which is transverse to the said transverse direction of movement of the battery within the receptacle, and a sloping member is fixed within the receptacle in such a position that the said slide member in the battery engages the sloping member in the receptacle when the battery is inserted therein, to resist the otherwise permitted movement of the battery within the receptacle in a transverse direction.

12. An arrangement according to claim 1, in which substantially the whole of the battery fits in the receptacle so that when the battery is inserted in the receptacle an outer surface of the battery casing is substantially flush with a rim of the receptacle 13. An arrangement according to claim 12, positioned in a prosthesis so that the receptacle is positioned to define a recess in the outer surface of the prosthesis.

* * * * *